US007616998B2

(12) United States Patent  (10) Patent No.: US 7,616,998 B2
Nuttin et al.  (45) Date of Patent: Nov. 10, 2009

(54) ELECTRICAL STIMULATION OF STRUCTURES WITHIN THE BRAIN

(75) Inventors: Bart Nuttin, Rotselaar (BE); Frans L. H. Gielen, Eckelrade (NL); Paul B. Cosyns, Kortenberg (BE); Jan Gybels, Oud-Heverlee (BE); Bjorn Meyerson, Bjurshom (SE); Per Mindus, Danderyd (SE); Marianne Wilof-Mindus, legal representative, Danderyd (SE)

(73) Assignee: Medtronic, Inc., Minneapolis, MN (US)

( * ) Notice: Subject to any disclaimer, the term of this patent is extended or adjusted under 35 U.S.C. 154(b) by 705 days.

(21) Appl. No.: 10/888,807

(22) Filed: Jul. 9, 2004

(65) Prior Publication Data

US 2005/0049650 A1  Mar. 3, 2005

Related U.S. Application Data

(63) Continuation of application No. 10/003,934, filed on Oct. 30, 2001, now Pat. No. 6,871,098.

(60) Provisional application No. 60/244,244, filed on Oct. 30, 2000, provisional application No. 60/244,378, filed on Oct. 30, 2000.

(51) Int. Cl.
*A61N 1/00* (2006.01)

(52) U.S. Cl. .......................................... 607/45

(58) Field of Classification Search ............... 607/45
See application file for complete search history.

(56) References Cited

U.S. PATENT DOCUMENTS 3,850,161 A  11/1974  Liss (Continued)

FOREIGN PATENT DOCUMENTS

WO  WO 94/01166  1/1994

OTHER PUBLICATIONS

Mueller et al., "Skin Impedance in Relation to Pain Threshold Testing by Electrical Means," Journal of Applied Physiology, vol. 5, pp. 746-752, 1953.

(Continued)

*Primary Examiner*—Scott M Getzow
(74) *Attorney, Agent, or Firm*—Shumaker & Sieffert, P.A.

(57) ABSTRACT

A method for treating a patient with an obsession, a compulsion, an anxiety or a depression disorder, comprising applying chronic electrical stimulation to at least a portion of the patient's anterior limb of the internal capsule under conditions effective to provide the patient with at least a partial relief from obsession and/or compulsion and/or anxiety and/or depression, by means of an electrical signal generator and at least an implantable electrode having a proximal end coupled to the said signal generator and a stimulation end capable of applying said chronic electrical stimulation, wherein the distance between the two outer contacts of the electrode corresponds to the depth of the internal capsule.

A method is disclosed for treating a patient with an obsession, a compulsion, an anxiety or a depression disorder. The method comprises applying electrical stimulation to at least a portion of the patient's anterior limb of the internal capsule or its surrounding structures including but not limited to the head of the caudate nucleus, putamen and nucleus accumbens. The electrical stimulation is applied by means of an electrical signal generator and at least an implantable electrode having a proximal end coupled to the signal generator and a stimulation end capable of applying electrical stimulation to the tissue.

28 Claims, 12 Drawing Sheets

U.S. PATENT DOCUMENTS

| | | | |
|---|---|---|---|
| 4,346,709 | A | 8/1982 | Schmitt |
| 4,596,807 | A | 6/1986 | Crosby |
| 4,692,147 | A | 9/1987 | Duggan |
| 4,698,342 | A | 10/1987 | Crosby |
| 4,867,164 | A | 9/1989 | Zabara |
| 4,892,538 | A | 1/1990 | Aebischer et al. |
| 4,912,126 | A | 3/1990 | Owen |
| 4,980,174 | A | 12/1990 | Sagen et al. |
| 5,025,807 | A | 6/1991 | Zabara |
| 5,084,007 | A | 1/1992 | Malin et al. |
| 5,119,832 | A | 6/1992 | Xavier |
| 5,186,170 | A * | 2/1993 | Varrichio et al. .............. 607/45 |
| 5,259,387 | A | 11/1993 | dePinto |
| 5,280,793 | A | 1/1994 | Rosenfeld |
| 5,299,569 | A | 4/1994 | Wernicke et al. |
| 5,330,768 | A | 7/1994 | Park et al. |
| 5,423,877 | A | 6/1995 | Mackey |
| 5,458,629 | A | 10/1995 | Baudino et al. |
| 5,458,631 | A | 10/1995 | Xavier |
| 5,470,846 | A | 11/1995 | Sandyk |
| 5,540,734 | A | 7/1996 | Zabara |
| 5,599,560 | A | 2/1997 | Siuciak |
| 5,711,316 | A | 1/1998 | Elsberry et al. |
| 5,833,709 | A | 11/1998 | Rise et al. |
| 5,938,688 | A | 8/1999 | Schiff |
| 5,975,085 | A | 11/1999 | Rise |
| 6,128,537 | A | 10/2000 | Rise |
| 6,167,311 | A | 12/2000 | Rezai |
| 6,176,242 | B1 | 1/2001 | Rise |
| 6,253,109 | B1 | 6/2001 | Gielen |
| 6,263,237 | B1 | 7/2001 | Rise |
| 6,353,762 | B1 | 3/2002 | Baudino et al. |
| 6,418,344 | B1 | 7/2002 | Rezai et al. |
| 6,516,231 | B1 * | 2/2003 | Flammang .................. 607/122 |
| 6,609,030 | B1 | 8/2003 | Rezai et al. |
| 6,782,292 | B2 | 8/2004 | Whitehurst |
| 2001/0003799 | A1 | 6/2001 | Boveja |

OTHER PUBLICATIONS

Laitinen et al., "Intraoperative Electrical Stimulation of the Brain in Patients with Obsessive-Compulsive Neurosis," Appl. Neurophysiol. 51(6): pp. 317-323, Nov.-Dec. (1988).

Andy, OJ, "Thalamic Stimulation for Control of Movement Disorders," Applied Neurophysiology, 46, pp. 107-111 (1983).

Alexander et al., "Functional Architecture of Basal Ganglia Circuits," Neural Substrates of Parallel Processing, TINS, vol. 13, No. 7, pp. 266-276 (1990).

Graham, et al., "Injection of Ecitatory Amno Acid Antagonists into the Medial Pallidal Segment of A 1-methyl-4-phenyl-1,2,3,6-tetrahydropyridine (MPTP) Treated Primate Reverses Motor Symptoms of Parkinsonism," Life Sciences, vol. 47, pp. PL-91-PL-97 (1990).

Crossman, et al., "Experimental Hemiballismus in the Baboon Produced by Injection of a Gamma-Aminobutyric Acid Antagonist into the Basal Ganglia" Neuroscience Letters, 20 pp. 369-372 (1980).

Duncan, et al., "Thalamic VPM Nucleus in the Behaving Monkey. III. Effects of Reversible Inactivation by Lidocaine on Thermal and Mechanical Discrimination," Journal of Neurophysiology vol. 70, No. 5, pp. 2086-2096 (1993).

Bobo, et al., "Convection-Enhanced Delivery of Macromolecules in the Brain," Proc. Natl., Acad. Sci USA, vol. 91, Applied Biological Sciences, pp. 2076-2080, Mar. (1994).

van Horne, et al., "Multichannel Semiconductor-Based Electrodes for in Vivo Electrochemical and Electrophysiological Studies in Rat CNS," Neuroscience Letters, 120, pp. 249-252, (1990).

Benabid, et al., "Long-term Suppression of Tremor by Chronic Stimulation of the Ventral Intermediate Thalamic Nucleus," The Lancet, vol. 337, pp. 403-406, Feb. (1991).

Martinez et al., "Toxicology Kinetics of Long-Term Intraventricular Infusion of Phenytoin and Valproic Acid in Pigs: Experimental Study," Acta Neurochirurgica Suppl. 52, pp. 3-4, (1991).

Medtronic SynchroMede® EL Infusion System.

Medtronic Itrel II Implantable Pulse Generator (IPG) Model 7424.

Harris Corporation Model CDP 1978 Frequency Generator.

B. Nuttin et al., "Electrical stimulation in anterior limbs of internal capsules in patients with obsessive-compulsive disorder," *Research Letters*, vol. 354, No. 9189, Oct. 30, 1999, 2 pages.

W.A.H. Rushton, "The Effect Upon the Threshold for Nervous Excitation of the Length of Nerve Exposed, and the Angle Between Current and Nerve," J. Physiol., 63(4), pp. 357-377, Sep. 9, 1927.

Lauri V. Laitinen, "Stereotactic Lesions in the Knee of the Corpus Callosum in the Treatment of Emotional Disorders," The Lancet, 1(7748), pp. 472-475, Feb. 26, 1972.

* cited by examiner

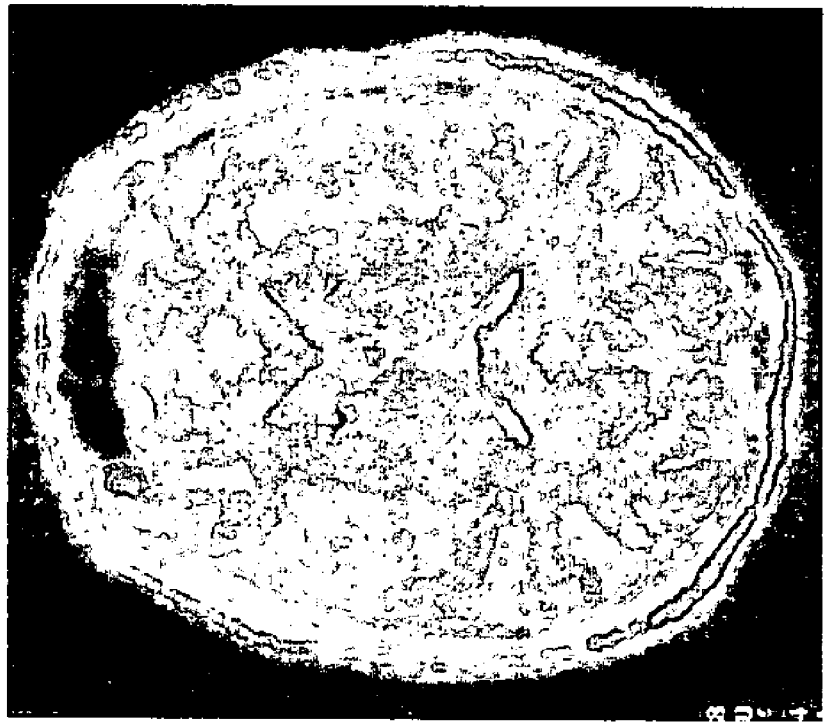

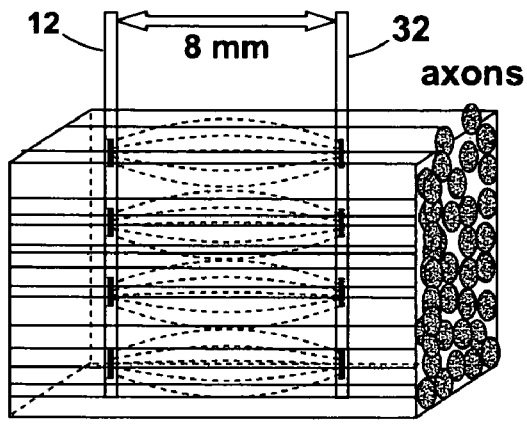
FIG. 6
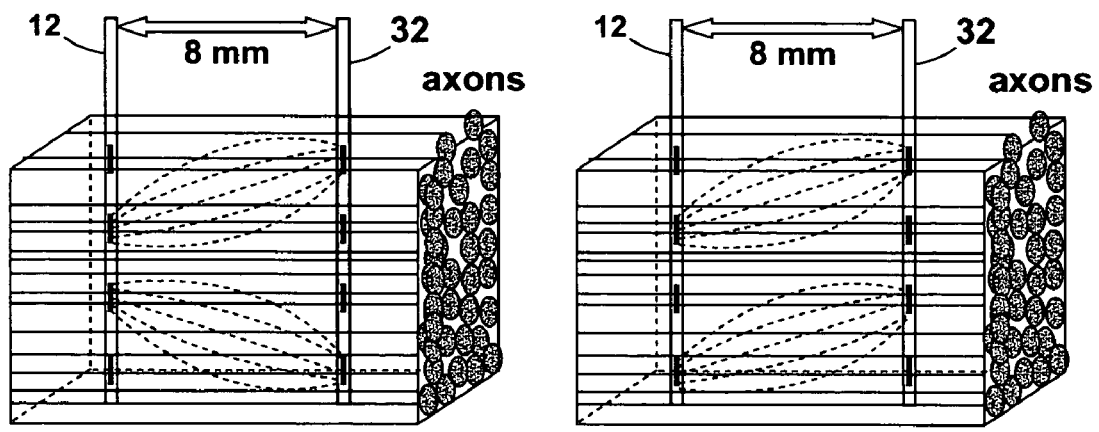
FIG. 7  FIG. 8

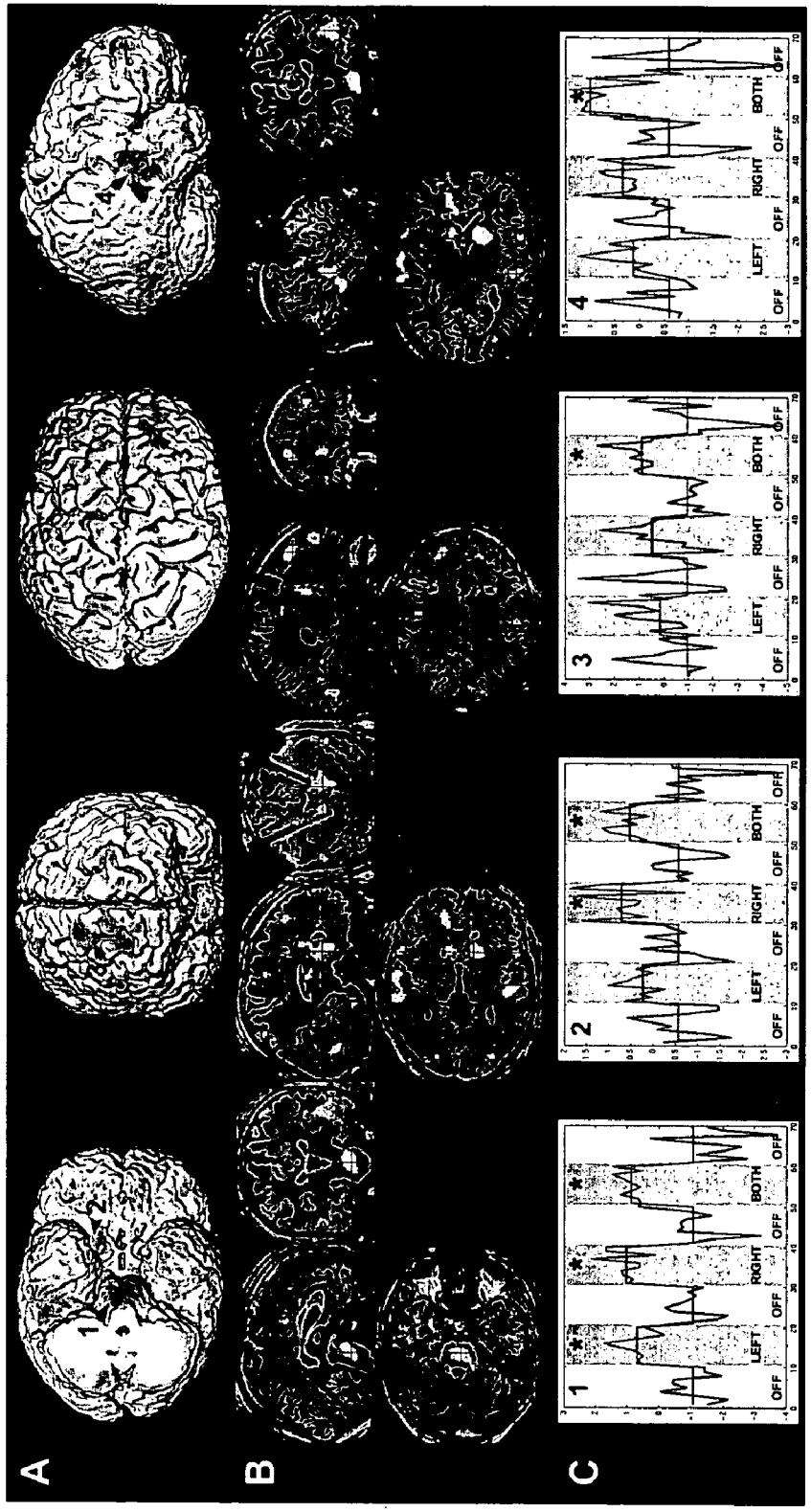

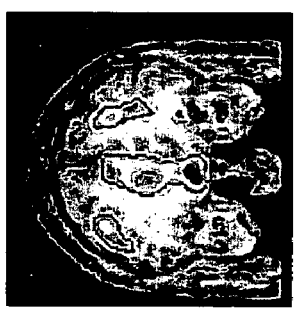
FIG.15A
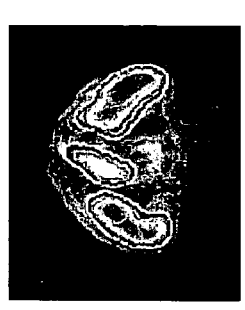
FIG.15B
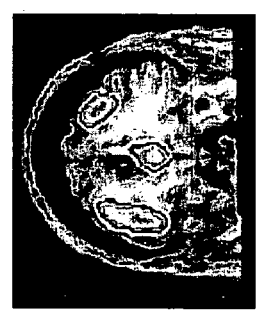
FIG.15C
FIG.16A
FIG.16B
FIG.16C

ELECTRICAL STIMULATION OF STRUCTURES WITHIN THE BRAIN

RELATED APPLICATIONS

This application is a continuation of U.S. application Ser. No. 10/003,934, filed Oct. 30, 2001 now U.S. Pat. No. 6,871,098, which in turn claims the benefit of provisional U.S. Application No. 60/244,244, filed Oct. 30, 2000, and provisional U.S. Application No. 60/244,378, filed Oct. 30, 2000. Each of these related applications is incorporated herein by reference in its entirety.

FIELD OF THE INVENTION

The present invention relates to the treatment of disorders of the central nervous system. More specifically the invention relates to a reversible method for the treatment of patients with obsessive-compulsive disorder and to a device for carrying out such a method.

BACKGROUND OF THE INVENTION

According to *Diagnostic and Statistical Manual of Mental Disorders* 4$^{th}$ ed. (American Psychiatric Association), obsessions are persistent ideas, thoughts, impulses or images that are experienced as intrusive and inappropriate and that cause marked anxiety or distress. They are intrusive because they interrupt the normal flow of thinking, dominating all other thoughts and the patient cannot control them. The patient struggles in vain to resist his obsessions, which can take up a great mount of time and energy, but usually the more resistant he/she is, the more strongly these thoughts come back. As opposed to psychotic disorders, they are contrary to the patient's very nature and he/she remains aware that these thoughts do not make sense and are a product of his/her mind. Most common obsessions include: thoughts about contamination, e.g. an excessive fear of dirt, germs, bodily fluids, dust, etc.; repeated doubts, e.g. about having done something or not, or about fearing to harm somebody; need to have things in a particular order, e.g. with perfect symmetry; aggressive or horrific impulses and images; and, sexual or pornographic images.

Together with these obsessions the patient may feel driven to compulsions, i.e., to repetitive behaviors or mental acts that are clearly excessive, in order to prevent some feared event or imagined danger becoming a reality. The most common forms of compulsive behavior are washing, cleaning, checking, requesting reassurance, hoarding, repeating, ordering, which can be time-consuming and interfere with the daily routine. The most common mental compulsions are counterimages, counting, rumination, and repeating prayers or words. A patient may suffer from one or more types of obsessions and compulsions at the same time. These obsessions and compulsions only become matters of clinical concern when their intensity and/or frequency cause marked distress, are time-consuming or significantly interfere with normal life, e.g. disrupting daily routines so much that working and concentrating correctly, taking part in social activities, or enjoying relationships with others becomes problematic.

Obsessive-Compulsive Disorder (hereinafter OCD), such as above defined, is a chronic psychiatric disorder with a worldwide lifetime prevalence rate of about 2.5%, according to P. Bebbington in *Br.J.Psychiatry* (1998) 173:2-6. The rate for OCD in first-degree relatives of OCD individuals is even above 10%. The rate for OCD is also higher for monozygotic twins than for dizygotic twins. The onset of OCD is usually earlier in males (between 6 and 15 years) than in females (between 20 and 29 years). Drugs that help OCD are classified as antidepressants, e.g. clomipramine (a serotonin-uptake inhibitor) and selective serotonin-uptake inhibitors (hereinafter SSRI) such as fluoxetine, fluvoxamine, sertraline and paroxetine. However, although about 60% of OCD patients have at least a moderate response to such medication, unfortunately at least 20% of OCD patients have no response at all to any of these drugs and fewer than 20% of those treated with such medication alone end up with no OCD symptoms. Moreover, the above-mentioned drugs have numerous side effects including nausea, drowsiness, insomnia, dry mouth and sexual dysfunction.

Clomipramine is even lethal in overdose. Another disadvantage of SSRIs is their ability to interact with other medications metabolized in the liver, thus either increasing side effects or inhibiting therapeutic benefits. Further, since the long-term effects of these drugs on a fetus are not yet clearly understood, giving such anti-obsessional medication to pregnant or breast-feeding women is usually avoided. According to most studies, a significant improvement in OCD symptoms is not noticeable until 6 to 10 weeks after starting SSRI treatment. Although some patients are able to discontinue medications after a six to twelve month period without relapsing, it is usually reasonable to stay on a full therapeutic dose for at least six months after OCD symptoms have been brought under control.

Some OCD patients may be helped with behavioral therapy, and often this kind of therapy is associated with the pharmacological treatment. Electro-Convulsive Therapy (ECT) is another alternative therapy, but only a few OCD patients improve thereafter.

In spite of the development of the above-mentioned therapies, a small, but significant proportion of OCD patients remain totally resistant to them. Furthermore, due to the side effects of the drugs and to the long-term treatment needed to ascertain the reality of symptom relief, some patients are discouraged because of the delay in improvement while side effects appear first and therefore tend to discontinue treatment at an early stage. A few of these patients, who are extremely ill and severely incapacitated, are candidates for neuro-surgical treatment.

Surgery for mental disorders is still a controversial issue partly due to the lack of randomized and double-blind controlled studies. However, neurosurgeons have been at least partially successful in treating chronic anxiety disorders by creating surgical lesions at specific locations in the neural circuitry of the brain that controls anxiety. For instance, there are numerous clinical reports substantiating that small and precisely placed lesions produced with stereotactic neurosurgical technique in specific regions of the brain (the anterior limbs of the internal capsules, the cingulum and the medial frontal subcaudate white matter) may ameliorate chronic and incapacitating OCD symptoms, as disclosed e.g. by Cosyns et al. in *Adv.tech.Stand.Neurosurg.* (1994) 21:239-279 and Lippitz et al. in *Acta Neuroch. Suppl.* (1997) 68:61-63. For the most part, these surgical procedures result in a destruction of the fiber pathways connecting various regions of the nervous system included in the list given above. Such a surgical treatment carries a low risk of complications and side effects but an obvious drawback is the irreversibility of a permanent lesion produced in the brain as documented by Stagno et al. in *The Journal of clinical ethics* (1994) 5(3):217-223 and by E.Hundert in *The Journal of clinical ethics* (1994) 5(3):264-266.

U.S. Pat. No. 6,128,537 "Techniques For Treating Anxiety By Brain Stimulation And Drug Infusion" by Rise issued Oct.

3, 2000 discloses using electrical stimulation in a nearly continuous manner to treat an anxiety disorder, e.g. by means of an implantable signal generator and an implantable electrode having a proximal end coupled to the signal generator and having a stimulation portion for electrically stimulating a predetermined stimulation site in the brain tissue. This patent discloses the following criteria for treatment of anxiety. Electrical stimulation of neural tissue may be implemented by providing pulses to two electrodes preferably having amplitudes of 0.1 to 20 volts, pulse widths varying from 0.02 to 1.5 milliseconds and repetition rates preferably varying from 2 to 2,500 Hz. An appropriate stimulation for use in connection with the anterior limb of the internal capsule is a high frequency stimulation, which aims at decreasing the neuronal activity in that portion of the brain. Enhanced results can be obtained by using a closed-loop system incorporating a sensor suitable for detecting symptoms of the disorder being treated, for instance a physiological signal related to heart rate, respiration rate, blood gases, galvanic skin response or muscle tension, the detected symptom being used to provide feedback to the patient to adjust stimulation parameters. The efficacy of treatment is enhanced if the neural tissue is stimulated while drugs such as GABA agonists are being administered by means of a pump implanted below the skin of the patient.

There is a need in the art for a method of treatment of OCD disorders which is safe and reversible and which provides the OCD patient with an effective relief from most OCD symptoms within a reasonable period of time while at the same time avoiding the various side effects of anti-depressant drugs such as clomipramine, SSRIs and GABA agonists.

BRIEF SUMMARY OF THE INVENTION

A method is disclosed for treating a patient with an obsession, a compulsion, or an anxiety or depression disorder comprising applying electrical stimulation to at least a portion of the patient's anterior limb of the internal capsule or immediately surrounding structures including but not limited to the head of the caudate nucleus, putamen or nucleus accumbens. This electrical stimulation is provided by means of an electrical signal generator and an implantable electrode having a proximal end coupled to the signal generator and a stimulation end capable of applying electric stimulation to at least a portion of the patient's anterior limb of the internal capsule to produce a significant change in neuronal activity in cortical and subcortical structures. In one embodiment of the invention, the change in neuronal activity resulting from stimulation is measured by functional magnetic resonance imaging to confirm the efficacy of the stimulation.

In another embodiment of the invention, at least a first lead having at least a first proximal electrode and at least a first distal electrode is placed in an internal capsule anterior portion. The first lead is connected to a neurological stimulator. The first proximal electrode and the first distal electrode are configured in a manner to deliver a stimulation signal generally parallel to axons in the internal capsule. The stimulation signal is delivered to the first proximal electrode and the first distal electrode. Internal capsule anterior portion neural activity is modulated to disrupt neural activity in the internal capsule anterior portion.

BRIEF DESCRIPTION OF THE DRAWINGS

FIG. 2A shows an axial Magnetic Resonance Image (MRI) of the brain with stimulation lead electrodes in the anterior limb of the internal capsule embodiment;

FIG. 2B shows a coronal MRI of the brain with stimulation lead electrodes in the anterior limb of the internal capsule embodiment;

FIG. 6 shows two stimulation leads placed in the internal capsule embodiment;

FIG. 7 shows two stimulation leads with an electrode configuration embodiment;

FIG. 8 shows another two stimulation leads with an electrode configuration embodiment;

FIGS. 11A-11B show cortical and subcortical functional MRI (fMRI) after subtracting brain activity during no stimulation from brain activity during stimulation superimposed onto surface reconstructions (FIG. 11A) and sections of the brain (FIG. 11B) with the left hemisphere shown on the right or bottom;

FIG. 11C shows a graph of the percent fMRI signal change (continuous line) and the statistically modeled signal change (dotted line) during left stimulation, right stimulation, both left and right stimulation, and no stimulation in the areas shown in FIGS. 11A-11B;

FIGS. 12A-12B show cortical and subcortical functional MRI (fMRI) after subtracting brain activity during no stimulation from brain activity during stimulation superimposed onto surface reconstructions (FIG. 12A) and sections of the brain (FIG. 12B) with the left hemisphere shown on the right or bottom;

FIG. 12C shows a graph of the percent fMRI signal change (continuous line) and the statistically modeled signal change (dotted line) during left stimulation, right stimulation, both left and right stimulation, and no stimulation in the areas shown in FIGS. 12A-12B;

FIGS. 13A-13B show cortical and subcortical functional MRI (fMRI) after subtracting brain activity during no stimulation from brain activity during stimulation superimposed onto surface reconstructions (FIG. 13A) and sections of the brain (FIG. 13B) with the left hemisphere shown on the right or bottom;

FIG. 13C shows a graph of the percent fMRI signal change (continuous line) and the statistically modeled signal change (dotted line) during left stimulation, right stimulation, both left and right stimulation, and no stimulation in the areas shown in FIGS. 13A-13B;

FIGS. 14A-14B show cortical and subcortical functional MRI (fMRI) after subtracting brain activity during no stimulation from brain activity during stimulation superimposed onto surface reconstructions (FIG. 14A) and sections of the brain (FIG. 14B) with the left hemisphere shown on the right or bottom;

FIG. 14C shows a graph of the percent fMRI signal change (continuous line) and the statistically modeled signal change (dotted line) during left stimulation, right stimulation, both left and right stimulation, and no stimulation in the areas shown in FIGS. 14A-14B; and, FIG. 15A-16C show Positron Emission Tomography (PET) images in three patients submitted to capsular stimulation.

DETAILED DESCRIPTION OF THE INVENTION

Figure 1A:
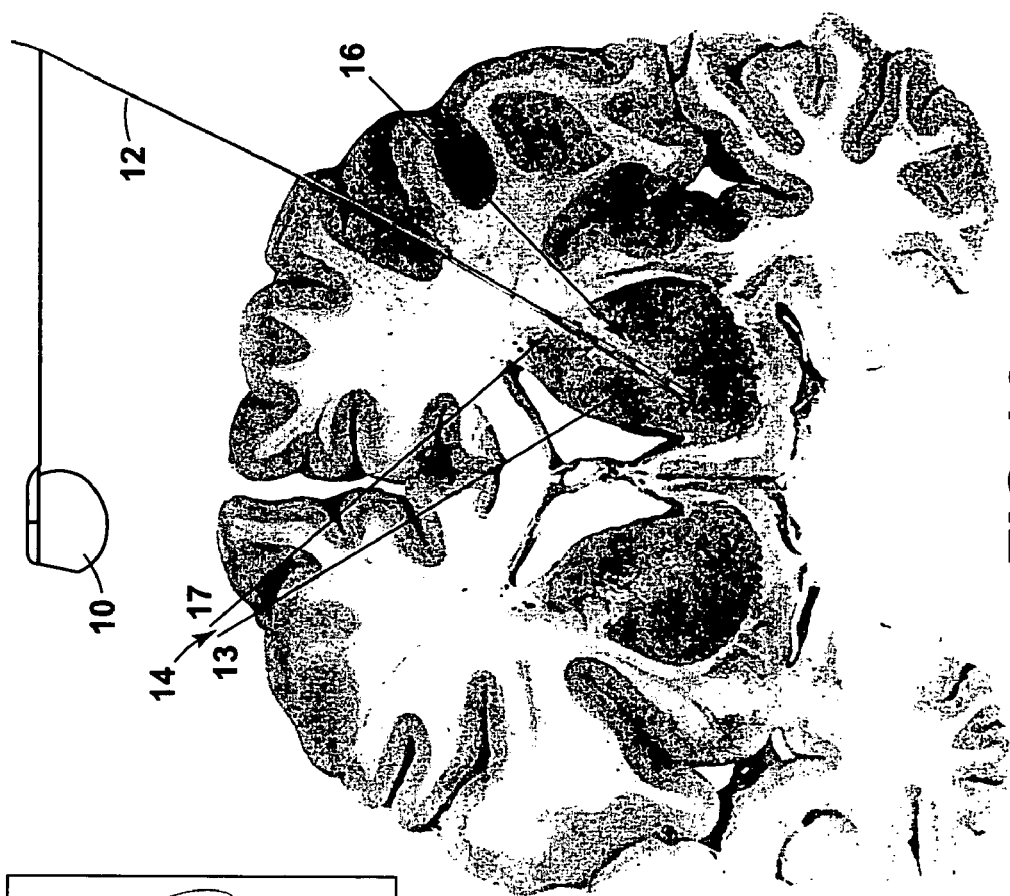
FIG. 1A shows a coronal cross-sectional view of a stimulation lead placed in the internal capsule embodiment.
Figure 1B:
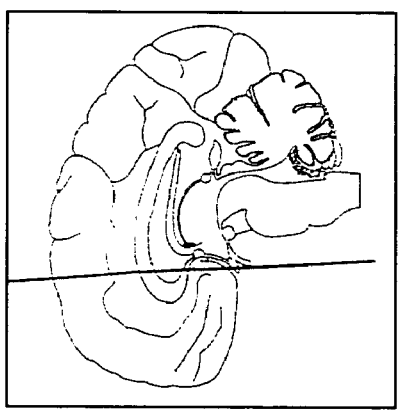
FIG. 1B shows a sagittal cross-sectional view of the brain illustrating the location of the coronal cross-section of FIG. 1A.

FIG. 1A shows a coronal cross-sectional view of a stimulation lead placed in the internal capsule embodiment and FIG. 1B shows a sagittal cross-sectional view of the brain illustrating the location of the coronal cross-section of FIG. 1A. The method of the present invention for treating a patient with an obsession, a compulsion or an anxiety or depression disorder comprises applying electrical stimulation to at least a portion of the patient's anterior limb of the internal capsule or immediately surrounding structures including but not limited to the head of the caudate nucleus, putamen or nucleus accumbens. This electrical stimulation is preferably provided by means of an electrical signal generator 10 (also known as a neurological stimulator) and an implantable lead 12 (also know as a stimulation lead or a first lead). The lead 12 has a proximal end coupled to the signal generator 10 and a stimulation end having at least one electrode 14. At least one electrode 14 (also known as a contact) is placed in the patient's anterior limb of the internal capsule 16 or structures nearby including but not limited to the head of the caudate nucleus, putamen or nucleus accumbens.

In the preferred embodiment of the invention, the stimulation is applied chronically to the patient's anterior limb of the internal capsule or structures nearby through the signal generator 10 and lead 12. Further, the chronic electrical stimulation is preferably applied in pulses having an amplitude in the range of from about 0.5 volts to about 50 volts, a pulse width in the range from about 60 µs to about 5 msec and a frequency in the range from about 2 Hz to about 2000 Hz. Although the preferred embodiment has the stimulation applied chronically, the stimulation may also be applied acutely or periodically. Further, stimulation above or below the preferred amplitude, pulse width or frequency may also be applied as desired as will occur to those skilled in the art.

FIG. 2A shows an axial Magnetic Resonance Image (MRI) of the brain with stimulation lead electrodes in the anterior limb of the internal capsule embodiment. FIG. 2B shows a coronal MRI of the brain with stimulation lead electrodes in the anterior limb of the internal capsule embodiment. In one embodiment of the invention, the change in neuronal activity resulting from stimulation is measured by functional magnetic resonance imaging to confirm the efficacy of the stimulation. Further, the detected change in neuronal activity may also be used to feedback to the signal generator 10 to control the parameters of stimulation applied to the lead or even whether to apply stimulation at all.

In the case of treating an OCD disorder, the efficacy depends on the selection and design of an appropriate electrode and/or on a careful selection of the conditions of electrical stimulation. Experience has shown that the parameters given above for the amplitude, pulse width and frequency of the stimulation pulse have been particularly effective in treating OCD. In particular, experimentation has demonstrated that a voltage significantly below about 0.5 volts would provide an insufficient symptom relief, whereas a voltage significantly above about 50 volts would induce side effects being a source of discomfort for a significant proportion of patients.

With respect to the design of the implantable electrode to be used in the device for electrical stimulation of human brain tissue for the treatment of OCD disorders in humans, leads, such as are well understood in the art, for stimulating tissue of the brain are used. In the preferred embodiment, the distance between the two outer contacts of the implantable electrode corresponds to the depth of the internal capsule of the patient and, more specifically, that this distance be at most about 25 mm, preferably between about 17 and 21 mm. Electrical stimulation may be applied either bilaterally (i.e. simultaneously and symmetrically in both capsules) or unilaterally. The number of electrodes may be any number including, but not limited to from about one to about eight. In particular, the number of four electrodes has proved to be very effective in clinical trials.

The various embodiments of the present invention provide reversible therapy to treat the various disorders. This reversibility has the advantage over known therapies for OCD disorders that are not reversible, in particular lesioning procedures. Reversibility allows the therapy to be discontinued if it proves ineffective or if it produces unwanted side effects. Reversibility also enables the performance of double-blind studies, as demonstrated by the inventors, which was hardly possible with the lesioning technique. While testing bilateral electrical stimulation in the anterior limbs of the internal capsules, we have achieved long-term beneficial effects on the cardinal symptoms in patients with OCD disorders, long-term effects being defined as effects observed and maintained after a period of at least 21 months of electrical capsular stimulation treatment.

Figure 3:
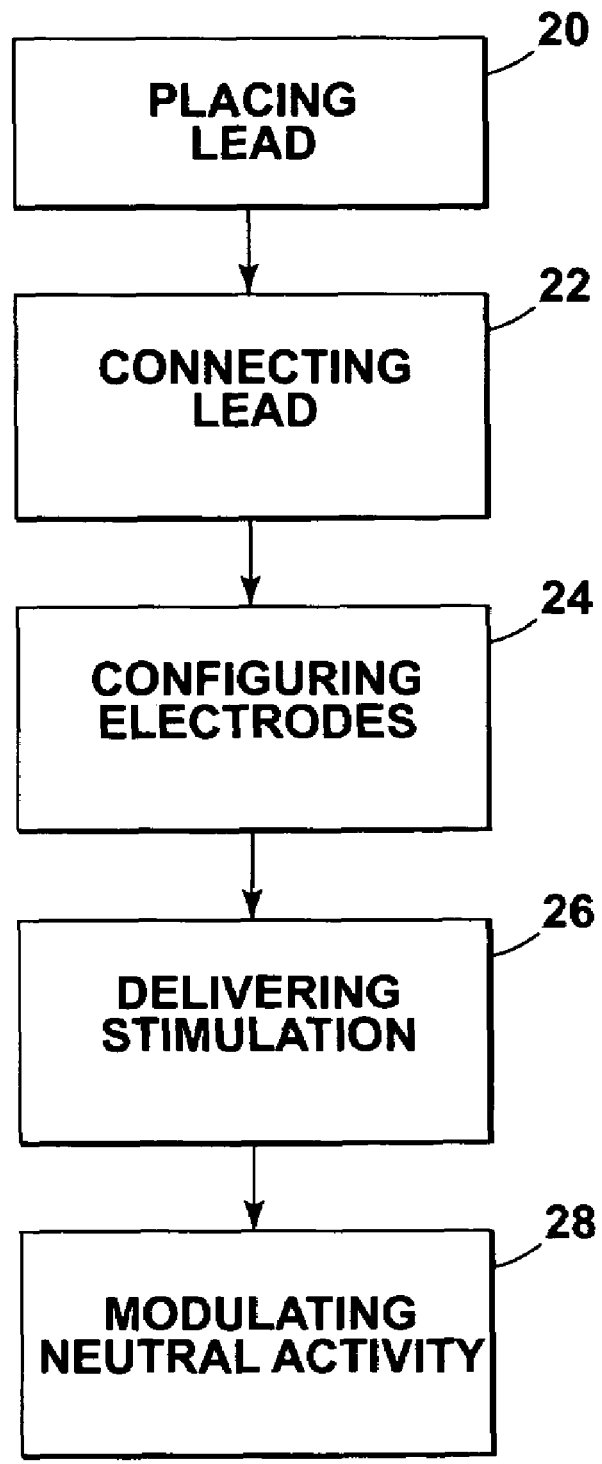
FIG. 3 shows a flowchart of another embodiment of a method for modulating brain internal capsule tissue to treat obsessive-compulsive disorder.

FIG. 3 shows a flowchart of another embodiment of a method for modulating brain internal capsule tissue to treat obsessive-compulsive disorder. The method 18 comprises the following elements. At least a first lead 12 (FIG. 1) having at least a first proximal electrode 17 and at least a first distal electrode 13 is placed in an internal capsule anterior portion 16. In some embodiments, a second lead 32 (FIG. 6) having at least a second proximal electrode and at least a second distal electrode is placed 20 in the internal capsule anterior portion 16. When a second lead is used, the first proximal electrode is spaced in the range from about 6 millimetres to about 10 millimetres from the second proximal electrode. The stimulation signal can be applied unilaterally to at least a portion of the patient's anterior limb of the internal capsule 16, or the stimulation signal is applied bilaterally to at least a portion of the patient's anterior limb of the internal capsule 16.

Figure 4:
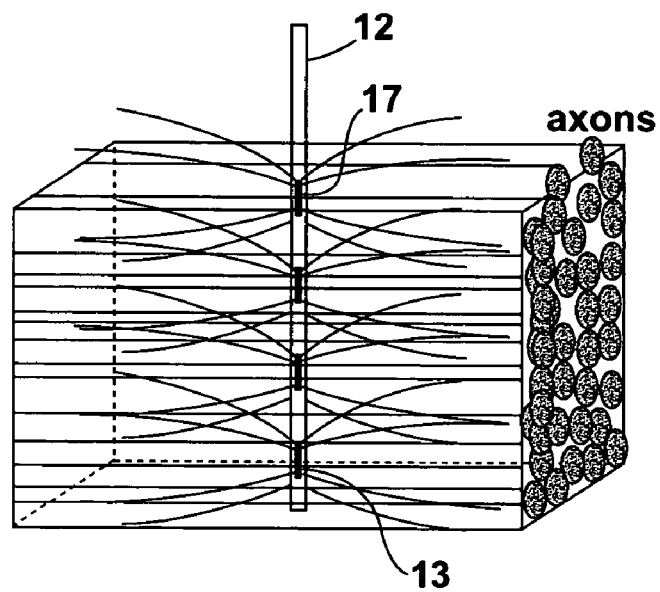
FIG. 4 shows one stimulation lead placed in anisotropic tissue of the anterior branch of the internal capsule embodiment.

FIG. 4 shows one stimulation lead 12 placed 20 (FIG. 3) in anisotropic tissue of the anterior branch of the internal capsule embodiment. As illustrated in FIG. 4, a distal portion of lead 12 that comprises electrodes, including electrodes 13 and 17 is implanted within the anterior internal capsule substantially perpendicular to the axons of the anterior internal capsule. The first lead 12 is connected 22 (FIG. 3) to a neurological stimulator 10. The first proximal electrode 17 and the first distal electrode 13 are configured 24 (FIG. 3) in a manner to deliver a stimulation signal generally parallel to axons in the internal capsule 16. The anterior internal capsule 16 contains (myelinated) axons, which run all approximately in the same direction. Biophysical arguments lead to the conclusion that the main direction of the stimulation currents should be parallel to these fibers in order to achieve the lowest possible threshold for modulation of activity in these fibers.

The first proximal electrode 17 and the first distal electrode 13 can be configured 24 as cathodes, and all other electrodes can be configured 24 as cathodes. The stimulation signal is delivered 26 (FIG. 3) to the first proximal electrode 17 and the first distal electrode 13. In some embodiments, the stimulation signal can also be delivered 26 to the second proximal electrode and the second distal electrode, and any or all other electrodes contained in the embodiment. The stimulation signal can have a voltage in the range from about 4 volts to about 12 volts, a pulse width in the range from about 200 µs to about 450 µs and a frequency in the range from about 50 Hz to about 200 Hz. By delivery of the neurostimulation signal, neural activity is modulated 28 (FIG. 3) in the internal capsule anterior portion 16 to disrupt neural activity in the internal capsule anterior portion 16.

Figure 5:
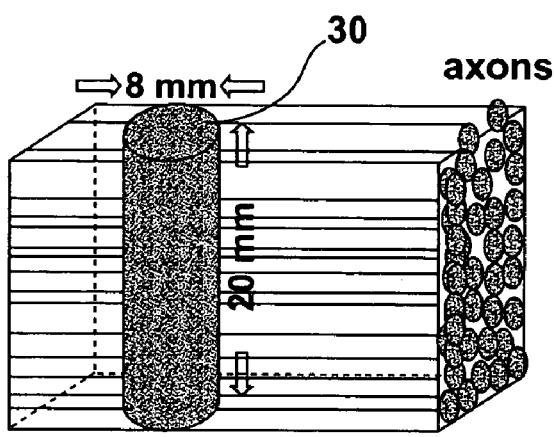
FIG. 5 shows a schematic of a Meyerson lesion in the lateral internal capsule.

FIG. 5 shows a schematic of a Meyerson lesion 30 in the anterior limb of the internal capsule. In some embodiments, the internal capsule anterior portion 16 Meyerson lesion 30 area can be modulated 28. Based upon the size of the Meyerson lesion (8 mm diameter and 20 mm long) for OCD and the direction of the lesion electrode trajectory (approximately perpendicular to the skull at the entry point anterior to the coronary suture) it was concluded that the length axis of the lesion is approximately perpendicular to the anterior capsule fibers. The depth of the internal capsule 16 is typically in the range from about 17 millimeters to about 21 millimeters. The modulated neural activity results in a significant increase in neuronal activity in a midline focus within the pons, as measured by functional Magnetic Resonance Imaging (fMRI).

FIG. 6 shows two stimulation leads placed in the internal capsule embodiment. As illustrated in FIG. 6, a distal portion of each of leads 12 and 32 that comprises electrodes is implanted within the anterior internal capsule substantially perpendicular to the axons of the anterior internal capsule. One technique to make use of stimulation current flow direction is to use a second lead 32 in addition to the first lead 12 in the internal capsule and stimulate between electrodes 14 that are on both leads. Doing this we have the opportunity to selectively modulate 28 sub bundles of the part of the anterior internal capsule 16, which is lesioned in the Meyerson method. Using the first lead 12 and the second lead 32 per side may increase the risk for bleeding with at least a factor two per side. The anterior part of the internal capsule 16 has a predominant axon direction. In biophysics, it is well described tat (stimulation) current runs approximately ten times better parallel than perpendicular to the axons in the brain (electrical anisotropy). As a consequence, such anisotropic tissues tend to redirect currents parallel to its axon direction. This implies that we may get our preferred current direction using only the first lead 12 with only negative electrodes 14 (also known as cathodes), while the case of the neurological stimulator 10, such as an Itrel II is positive.

FIGS. 7 and 8 show two stimulation leads with an electrode configuration embodiments. For embodiments using a first lead 12 and a second lead 32, a special bifurcated extension cable can be used. This cable allows us to stimulate with both the first lead 12 and the second lead 32 with only one Itrel II-like neurological stimulator 10. This type of stimulation is, however, typically limited to a maximum of four electrodes 14 of the eight possible electrodes 14 on the two implanted quadripolar leads. In principle, we would like to "modulate" the activity in the same volume of tissue that would be lesioned for OCD (FIG. 5). This consideration helps us make a choice for the lead to be used in this OCD project. The key argument is that the "spatial span" of the 4 electrodes should allow us to stimulate the whole area that would be lesioned (FIG. 5). An example of a stimulation lead that would be acceptable for modulating 28 neural activity in the brain internal capsule anterior portion 16 is the Medtronic, Inc. Model 3887 stimulation lead that is marketed as a spinal cord stimulation lead.

Figure 9:
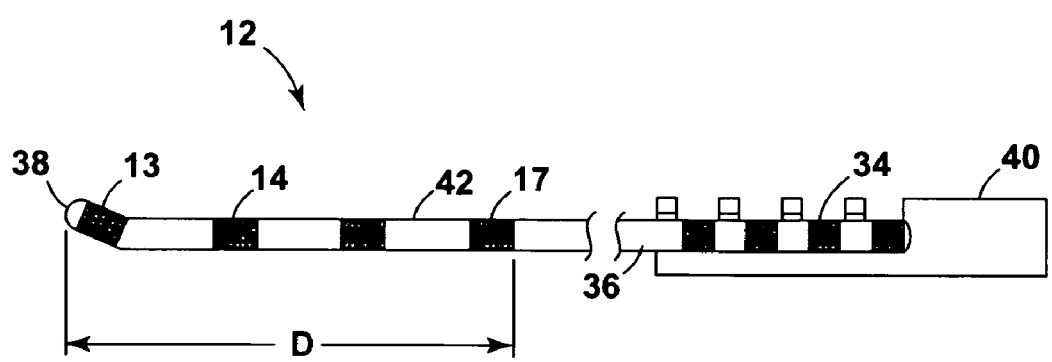
FIG. 9 shows a stimulation lead embodiment.
Figure 10A:
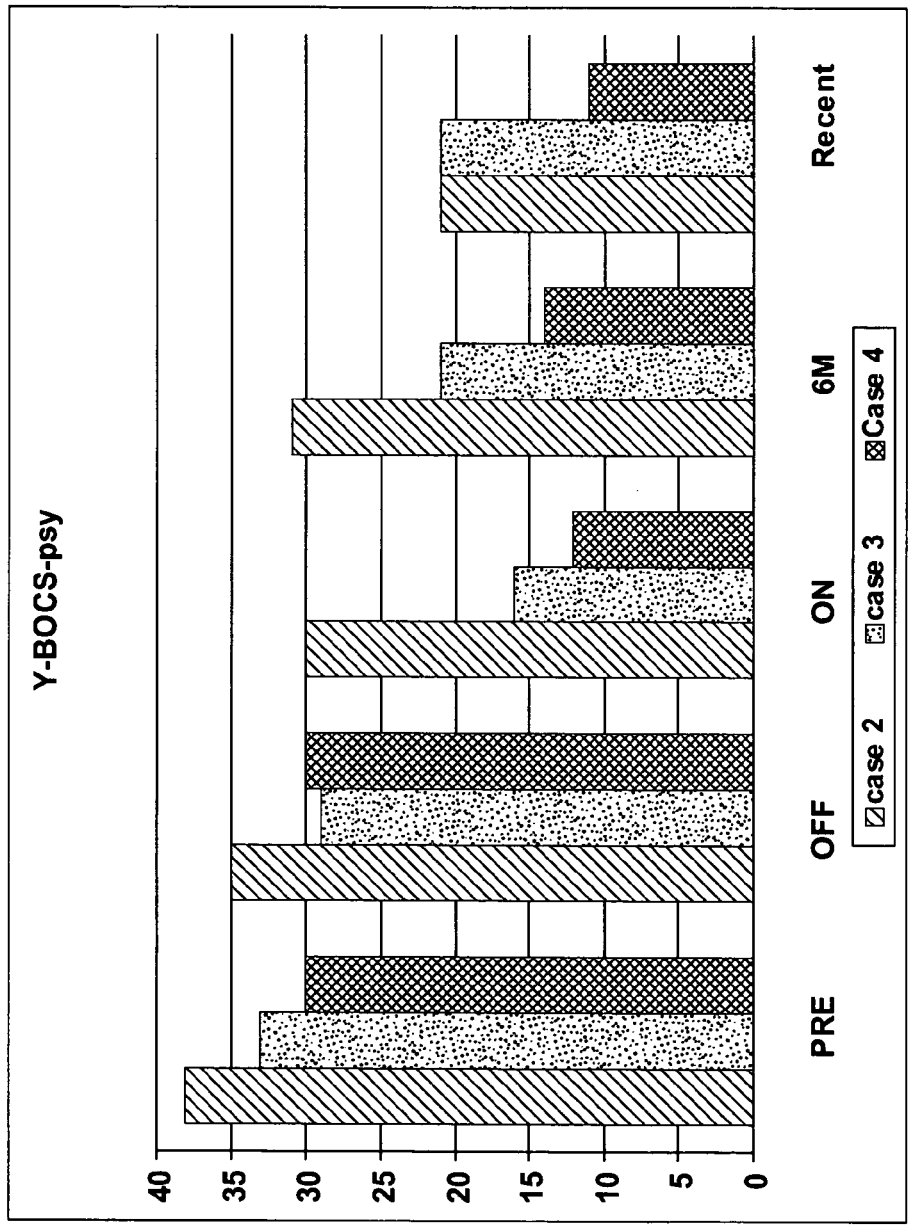
FIGS. 10A-10D show the results of four psychiatric assessment tests performed on three patients submitted to capsular stimulation.
Figure 10B:
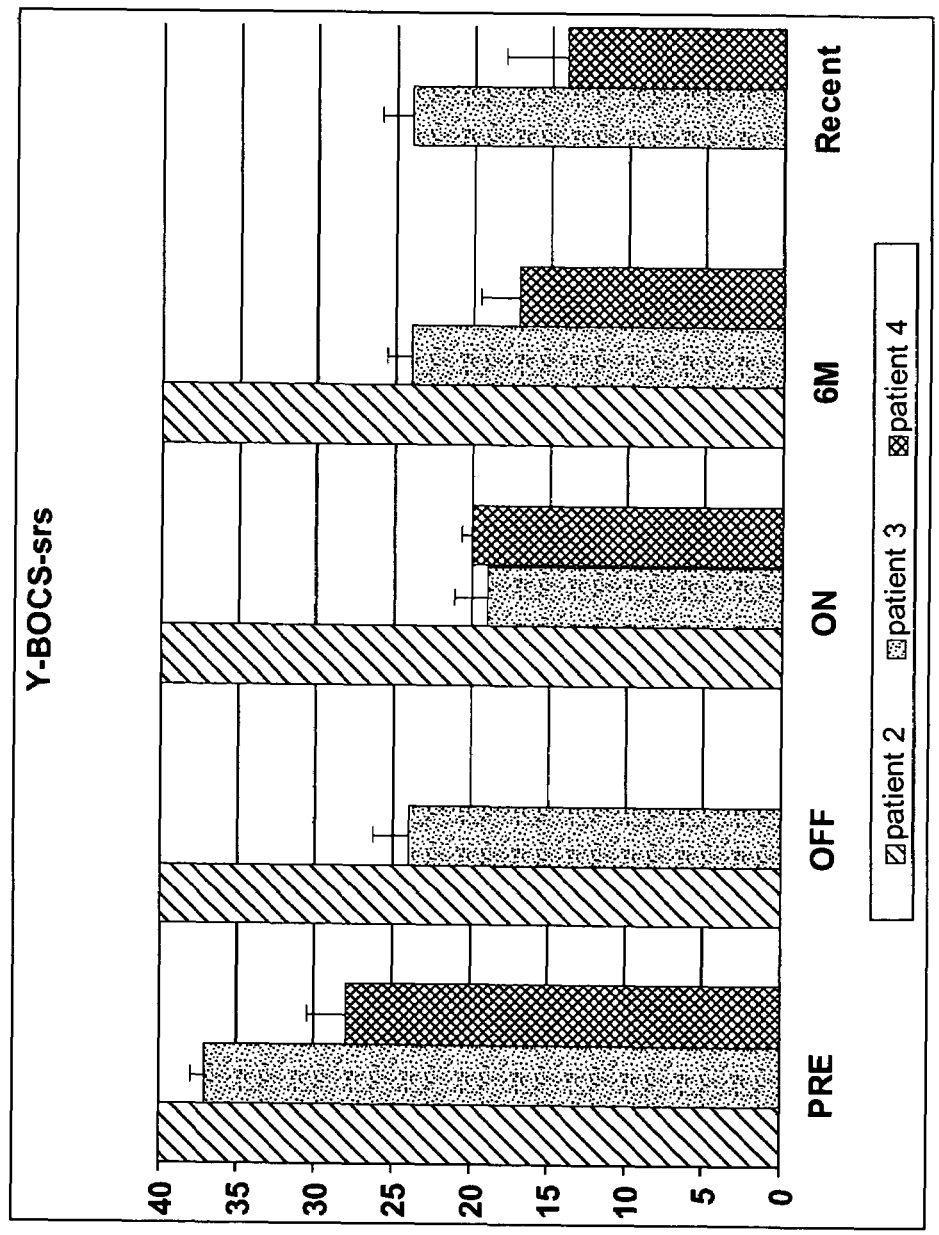
Figure 10C:
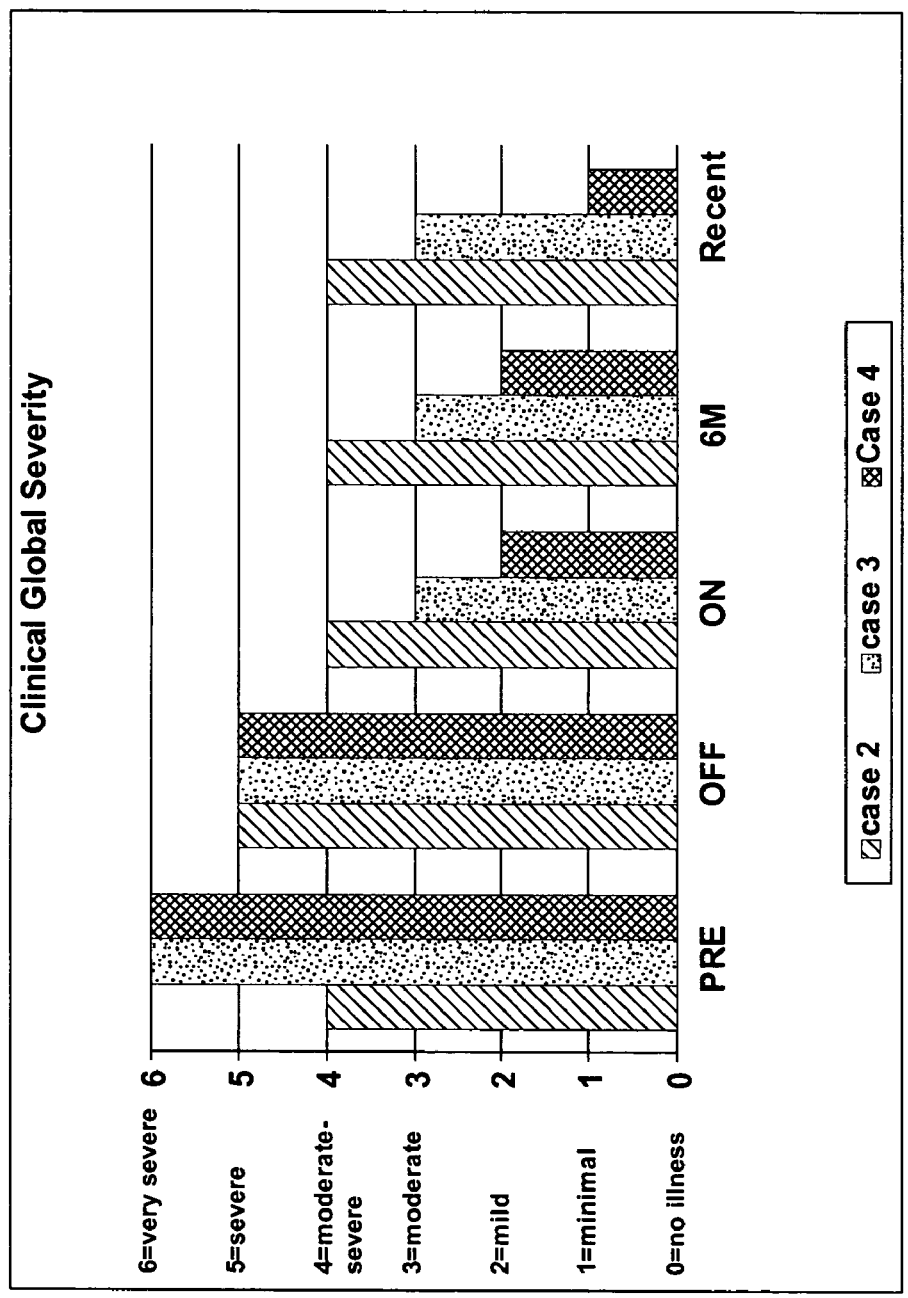
Figure 10D:
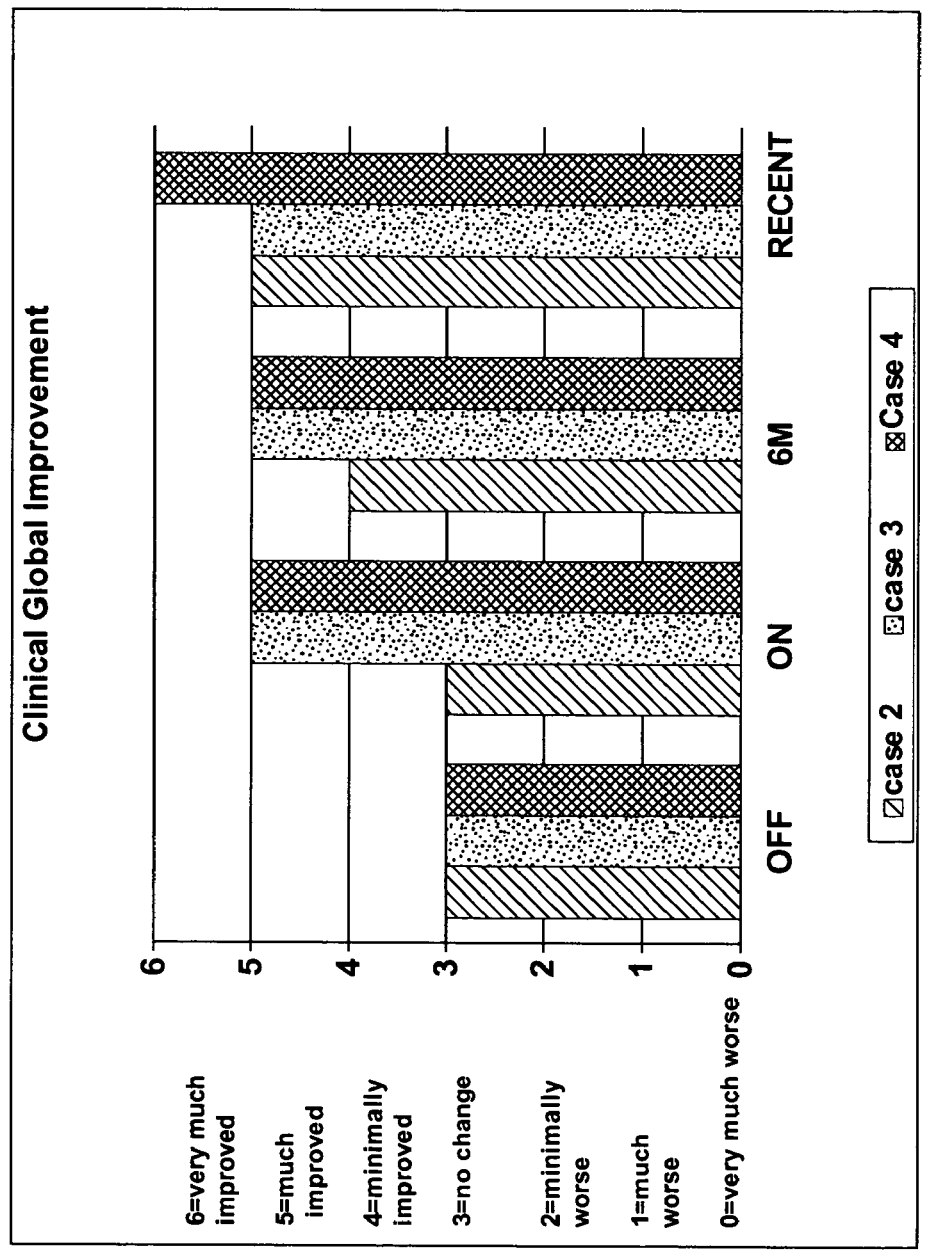

FIG. 9 shows another stimulation lead embodiment. This stimulation lead embodiment comprises at least one electrode 14, made from a noble metal such as platinum and/or iridium, placed on the stimulation end and connected at its proximal end, through a conducting connector 34, to a signal generator 10 (not represented on the figure). The device body 36 is made of a plastic material such as e.g. polyurethane. In this embodiment, it comprises a bend 38 at the stimulation end for helping the physician in positioning the lead 12 during surgical treatment, although the presence of such a bend 38 is not critical. The bending angle of bend 38 may be in the range from about 0 to about 30 degrees, preferably in the range of about 10 to about 25 degrees. It also comprises a handle 40 for the same practical consideration as above. In the embodiment represented herein, the lead 12 comprises four electrodes 14 spaced apart from each other by three spaces 42. The size and number of the electrodes 14 and spaces 42 is such that the distance D between the two outer electrodes 14 of the lead 12 corresponds to the depth (being defined as the dimension relative to midline of the brain) of the internal capsule 16 i.e., as said above, is at most 25 mm and more preferably between about 17 and 21 mm.

The invention will now be described by reference to the following non-limiting examples. Six patients were selected by two committees for neurosurgical interventions for psychiatric disorders and very strict selection criteria, according to Cosyns et al. (cited supra) and B. Meyerson in *Textbook of stereotactic and functional neurosurgery* (1998), Gildenberg and Tasker eds. (McGraw-Hill, New-York), were met. All patients fulfilled the criteria for OCD according to the *Diagnostic and statistical manual of psychiatric disorders* (cited supra). The interventions and clinical evaluations were performed at University Hospital of Leuven (Belgium), University Hospital of Antwerpen (Belgium) and at Karolinska Hospital (Stockholm, Sweden).

In patient one (to be considered as a comparative example for the reasons explained hereinafter), treated at Karolinska Hospital, two quadripolar leads 12 Model 3487A Pisces Quad® (6 mm spacing 42, 3 mm electrode 14 length, total distance D between the two outer electrodes 14 being about 30 mm, available from Medtronic Inc., Minneapolis, Minn., United States) were stereotactically implanted bilaterally into the anterior limbs of the internal capsules 16. In the other five patients (hereinafter patients two to six), two quadripolar leads 12 Model 3887 Pisces Quad Compact® (4 mm spacing 42, 3 mm electrode 14 length, total distance D between the two outer electrodes 14 being 24 mm, available from Medtronic Inc., Minneapolis, Minn., United States) were used. The selected stimulation targets in the internal capsules were the anterior limbs 16 thereof. The tips of the leads 12 were placed at the basal parts of the internal capsules as shown in FIG. 1A. Three of the stimulating electrodes 14 were placed in the internal capsule 16 and the fourth electrode 14 (the most proximal one, being farthest away from the electrode tip) was situated dorsally to the internal capsule 16. A symmetrical implantation of both electrodes 14 via precoronal burr holes was the aim. The interventions were performed under either general or local anesthesia with prophylactic antibiotics. After having performed postoperative electro-encephalography (EEG), magnetic resonance imaging (MRI) and, in patient six, functional magnetic resonance imaging (fMRI), the electrodes were connected to two implanted pulse generators 10 (Itrel® II, Synergy™ or Kinetra™, available from Medtronic Inc., Minneapolis, Minn., United States).

During all evaluation sessions the patients, evaluating psychiatrists and psychologists were blinded for stimulation conditions. During the first weeks or months after the operation (i.e., the immediately postoperative screening phase) patients were stimulated using different stimulation parameters (while keeping voltage in the range from about 0.5 volts to about 50 volts, pulse width in the range from about 60 μs to about 5 ms and frequency in the range from about 2 Hz to about 2000 Hz) and different contact combinations in order to determine optimal stimulation parameters. During the subsequent crossover period (stimulator "on" during three months, followed by stimulator "off" during three months or vice versa in random order), electrical stimulation was performed at a threshold level for obvious acute reduction of obsessive thoughts, depression and anxiety. Electrode 14 combinations with lowest threshold for these effects were used. Such thresholds could only be found in two patients. In two other patients, somewhat odd behaviors during stimulation were observed (e.g. suddenly and totally out of the context one patient said "I want French fries"). For those patients, the contact combination with lowest threshold for such response was used and stimulation was performed at threshold level for those effects. During the crossover period the surgeon adjusted the amplitude according to these criteria in acute stimulation. In the two other patients no immediate effects of stimulation were observed and stimulation during the screening period was applied with relatively high intensity (i.e., a voltage from about 5 to about 9 V) and with the three most ventral electrodes 14 connected as cathode and the stimulator case or the uppermost electrode 14 as anode. Stimulation was applied simultaneously and symmetrically in both capsules, i.e., bilaterally.

Postoperative technical investigations systematically included MRI. In patient six, fMRI was performed ten days postoperatively using a 2×3 factorial design with stimulation ("on" or "off") and electrode 14 side (left, right and both) as factors. Stimulation and non-stimulation epochs were alternated every 60 seconds during the acquisition of a series of 140 scans. Four such series were acquired in which the order of conditions (no stimulation, stimulation via left, right or both electrodes) was pseudo-randomised. Imaging was performed on a 1.5 tesla imager with gradient echo—echo planar imaging (TR/TE=3000/40 ms, FOV=$200^2$ mm$^2$, matrix=$64^2$, 32 transverse slices of 4 mm thickness). A statistical parametric map (hereinafter referred as SPM) 99 according to Friston et al. in *Hum. Brain Map* (1994) 1:153-171 was used for head motion correction, spatial normalization to a standard brain and spatial smoothing. The statistical data analysis was performed by modelling the different conditions as a box car function convolved with the hemodynamic response function, in the context of the general linear model as employed by SPM99. Global changes were adjusted by proportional scaling and low frequency confounding effects were removed by an appropriate high pass filter. Specific effects were tested by applying appropriate linear contrasts to the parameter estimates for each condition. The resulting t-statistic for each and every voxel constitutes an SPM with threshold at $p<0.05$ corrected for multiple comparisons.

Three patients who completed the blinded crossover design, as explained hereinafter, were subjected to Positron Emission Tomography (PET) both preoperatively within one month before surgery and postoperatively after three months of continued stimulation, using a Siemens HR+ apparatus. After positioning the patient on the camera, a transmission scan for attenuation correction was performed. Afterwards, 150 MBq of [$^{18}$F]-fluoro-deoxyglucose (FDG) was injected intravenously and the acquisition was performed between 30 and 60 minutes post injection in 3D mode. An EEG was performed during and immediately after capsular stimulation in order to test for epileptic activity due to stimulation. Psychiatric assessment included the following tests. Psychiatrist-rated Yale-Brown Obsessive Compulsive scale (hereinafter referred as Y-BOCS-psy) as disclosed by Goodman et al. in *Arch. Gen. Psychiatry* (1989) 46:1006-1016 and by Steketee et al. in *Behav. Res. Ther.* (1996) 34:675-684. Clinical Global Severity (hereinafter referred as CGS) and Clinical Global Improvement (hereinafter referred as CGI), both as disclosed by W. Guy in *Assessment Manual for Psychopharmacology* (1976) of the U.S. Department of Health. Profile of Mood State (hereinafter referred as POMS) as disclosed by McNair et al. in *manual of the profile of mood states* (1971) of Educational and Industrial testing Service (San Diego, Calif.). Tests were performed two weeks before surgery and at the end of each branch of the crossover design. It should be noted that the cross over designs described herein are only specific for a clinical study situation and should not specify or limit the invention description herein.

Tests were performed two weeks before surgery and at the end of each branch of the crossover design. Patients were asked to complete weekly a self-rating scale of the Y-BOCS (hereinafter referred as Y-BOCS-srs) and POMS tests beginning eight weeks before until one year after surgery. The study protocol was approved by both local hospital ethics committees and was in accordance with the Helsinki Declaration of 1975 (revision 1983). The follow-up period for the six patients who received a bilateral implant was respectively: 31 months for patient one; 26 months for patient two; 24 months for patient three; 21 months for patient four; 9 months for patient five; and, 4 months for patient six.

In five patients, patient two through patient six, in whom a Model 3887 Pisces Quad Compact™ lead 12 was implanted, at least some beneficial effects were seen. Acute and almost instantaneous stimulation effects, easily noticeable already without any validated psychiatric test, were most prominent in patients four and six. Patients three and five responded to the stimulation in a less conspicuous manner. However, no beneficial effects were seen at all in patient one who received a Model 3487A Pisces Quad™ lead 12, this being attributable to an unsuitable design of the said lead 12, in particular a too short distance between the two outer electrodes 14 of the lead 12. In patient two, electrical stimulation consumed so much energy that despite some limited beneficial effects (as shown in FIGS. 10A-10D) the electrodes were removed after 15 months. In patients one and two a bilateral anterior capsulotomy was then performed. In patient one this intervention was done before the start of the crossover design for ethical reasons and therefore this patient was excluded from further analysis. Evaluation during the immediate postoperative period clearly shows acute beneficial effects being induced by the capsule stimulation in patient five and patient six.

FIGS. 10A-10D show a finding summary of psychiatric assessment for the long-term treatment of patients two through patient four. These figures provide the ratings of patient two through patient four at pre-surgical baseline (PRE), in stimulator-on (ON) and stimulator-off (OFF) branch of the crossover design, after six months of continuous stimulation after crossover (6M) and most recent scores (RECENT), i.e., after 23 months in trial for patient three and after 21 months in trial for patient four. Y-BOCS-psy for patients 2 to 4 decreased during the blindly assessed stimulator-on branch. In two of them, a more than 35% reduction was noted at any time during stimulation and they are consequently considered as responders. Patient two was a non-responder. Patients three and four experienced and reported relief of OCD symptoms during the stimulator-on branch and their weekly Y-BOCS-srs scores dropped substantially. In both these patients, pretreatment CGS (FIG. 10C) was 6 (=extremely severe) while, with stimulation on, CGS rated 3 (=moderate) in patient three and patient two (=mild) in patient four. CGI (FIG. 2D) was 5 (=Much improved) for both patients. When the stimulator was off, Y-BOCS and CGS approached baseline level and CGI score was 3 (=no change). Symptom-relieving effects of stimulation remained obvious six months after start of the crossover and 21 months after implantation of the electrodes.

Tables 1-5 that follow show weekly POMS data reflected major individual differences in mood states, as shown in the following table reporting the effect of capsular stimulation on POMS-scores for depression (Table 1), fatigue (Table 2), anger (Table 3), vigor (Table 4) and tension (Table 5) in patients two through patient four who went through the crossover design and completed the twenty-one months of the study. Most marked mood-state variation for patient two was an increase in vigor in stimulator-off condition. Patient three had very high scores on all POMS sub-scales at baseline, with substantial decreases after surgery, regardless whether the stimulator was on or off. For patient four, complaints of increased fatigue when stimulator was on were reflected in marginally higher fatigue scores of the POMS and went paradoxically hand in hand with an increase in vigor. POMS scores for depression did not fully report the severe suicidal idea in stimulator off. This may be attributed to missing data of patient three who refused to return the weekly POMS when severely suicidal, and to the cessation of the stimulator-off period when dangerous suffering, despair and agony were patent.

TABLE 1

| Mean POMS (+/− SD) | | Depression Crossover Stimulator | Crossover Stimulator | Stimulator |
|---|---|---|---|---|
| Patient | Preoperatively | "On" | "Off" | "On"[1] |
| 2 | 28 (3.8) | 31 (2.2) | 30 (1.5) | 30 (2.7) |
| 3 | 40 (0.6) | 27 (2.8) | 28 (4.2)[3] | 31 (4.3) |
| 4 | 19 (3.2) | 17 (2.9) | 20[2] | 16 (1.7) |

TABLE 2

| Mean POMS (+/− SD) | | Fatigue Crossover Stimulator | Crossover Stimulator | Stimulator |
|---|---|---|---|---|
| Patient | Preoperativly | "On" | "Off" | "On"[1] |
| 2 | 27 (1.2) | 29 (1.2) | 28 (1.5) | 30 (0.7) |
| 3 | 29 (0.6) | 17 (0.7) | 19 (3.4)[3] | 22 (4.1) |
| 4 | 17 (3.2) | 19 (3.3) | 14[2] | 18 (1.2) |

TABLE 3

| Mean POMS (+/− SD) | | Anger Crossover Stimulator | Crossover Stimulator | Stimulator |
|---|---|---|---|---|
| Patient | Preoperatively | "On" | "Off" | "On"[1] |
| 2 | 13 (1.7) | 14 (5.0) | 15 (3.0) | 14 (3.3) |
| 3 | 23 (2.0) | 17 (2.8) | 15 (3.6)[3] | 17 (0.7) |
| 4 | 13 (1.0) | 12 (2.6) | 13[2] | 9 (2.1) |

TABLE 4

| Mean POMS (+/− SD) | | Vigour Crossover Stimulator | Crossover Stimulator | Stimulator |
|---|---|---|---|---|
| Patient | Preoperatively | "On" | "Off" | "On"[1] |
| 2 | 9 (0.6) | 9 (2.0) | 15 (1.6) | 10 (4.1) |
| 3 | 24 (0.6) | 13 (1.4) | 14 (4.0)[3] | 19 (2.0) |
| 4 | 11 (4.2) | 14 (1.4) | 9[2] | 15 (2.3) |

TABLE 5

| Mean POMS (+/− SD) | | Tension Crossover Stimulator | Crossover Stimulator | Stimulator |
|---|---|---|---|---|
| Patient | Preoperatively | "On" | "Off" | "On"[1] |
| 2 | 28 (0.6) | 27 (1.5) | 29 (1.4) | 29 (1.4) |
| 3 | 29 (0.6) | 21 (1.4) | 24 (4.7)[3] | 23 (4.0) |
| 4 | 19 (2.1) | 15 (1.8) | 21[3] | 15 (1.6) |

[1]evaluation six months after end of crossover following six months of continuous stimulation.
[2]only one data series stimulator "Off" proved intolerable after having experienced "On".
[3]missing data due to severe worsening and suicidal behaviour.

Although blinded for stimulation conditions, psychiatrists and psychologists noted a severe worsening of mood during the stimulator-off branch, and were alerted by suicidal thoughts in all three patients. The research team decided it was not ethical to let patients suffer and the off-period was abridged to five weeks (patient two) and ten weeks (patient three) respectively, depending on the moment of severe worsening. Patient four refused to support the dramatic return of her obsessions and compulsions when current supply was switched off, although she was unaware of the stimulation parameters. At the time when the stimulator battery was exhausted, the symptoms also returned with former intensity, but became not worse than before surgery.

In order to try to prolong the battery lifetime the stimulator 10 was switched "off" at night in two patients who received Synergy™ implanted pulse generators 10 after the crossover period was finished. However, one minute only after current supply was switched off automatically, they became extremely anxious, obsessed and depressed and they could not continue their sleep, although they were unaware of the programming status. During daytime they were stimulated and felt better but tired. These patients themselves explained their tiredness by having not slept at night and asked not to proceed further with this stimulation program. Two patients received a handheld programmer after the crossover period in order to enable them to adjust the stimulation amplitude. One of them decided to diminish the amplitude from 10 volts, when having social contacts, to 9.5 volts during the rest of the day and to 8.5 volts at night. Later on she was allowed to select her preferred pulse width between 210 and 450 μs. No clear signs of frontal-lobe type personality change or dysfunction were ever observed in any of the patients.

FIGS 11A-11B, 12A-12B, 13A-13B and 14A-14B show cortical and subcortical fMRI activation when subtracting brain activity during no stimulation from brain activity during stimulation, superimposed onto surface reconstructions (A) and sections of the patient's brain with the left hemisphere shown on the right or at the bottom (B). Regions are labelled as follows: 1=midline focus in the pons; 2=striatum; 3=focus in the right frontal cortex; and, 4=middle temporal gyrus. Functional magnetic resonance imaging (fMRI) was performed in patient six in order to visualize the neuronal substrate of short-term electrical stimulation of the anterior limbs of the internal capsule. Stimulation resulted in a significant increase in neuronal activity in several cortical and subcortical structures.

FIG. 11C, 12C, 13C and 14C shows the percent MRI signal change (continuous line) and statistically modeled signal change (dotted line) during left, right, simultaneous (BOTH) and no stimulation ("Off") in the four above labeled regions. Conditions for which stimulation versus no stimulation was significant ($p<0.05$ corrected for multiple comparisons) are indicated with (*). The strongest activation was located in a midline focus within the pons. The activity profile revealed that this region was almost equally active whether stimulation was delivered either uni- or bilaterally. Near the electrode tip, activity was found in left and right striatum. Finally, weaker activation was observed in right frontal cortex, in the superior and middle temporal gyrus, and in the lateral occipital cortex bilaterally (not shown), such activation being only significant when both stimulators were on simultaneously.

FIGS. 15A-16C show Positron Emission Tomography (PET) images in three patients (patients two through four) after subtraction analysis between PET images before implantation and after stimulation during a three month period. Subtraction analysis of postoperative and preoperative PET scans was performed and showed a marked decrease of frontal metabolism after three months of stimulation. The MRI scan and the preoperative and postoperative PET images were co-registered using an automated algorithm, as disclosed by Maes et al. in *IEEE transactions on medical imaging* (1997) 16:187-198, and subtracted after normalization for global counts. Only the voxels in the post-operative PET scan with a decreased glucose metabolism of more than two standard deviations are combined with the co-registered MRI scan (patients two and four) or with the pre-operative PET scan (patient three), the latter images being displayed in a gray scale. Left hemisphere is shown on the right. Epileptic activity could not be detected by EEG, neither during nor immediately after the end of the stimulation The above results show that bilateral electrical stimulation in the anterior limbs of the internal capsules induce a significant decrease in the Y-BOCS, both evaluated by the patient as well as by the psychiatrist. Although the patients were blinded to their stimulation condition, the Y-BOCS-psy scores return to higher levels when the stimulators are turned off. The results of the other standardized measures (CGS, CGI) follow the evolution of the Y-BOCS. But not all patients responded favorably, which is to be compared to the results after anterior capsulotomy as reported by Mindus et al. in *Psychat. Clin. North Amer.* (1992) 15:921-938. As shown by fMRI in one patient, it appears that the neuronal substrate of electrical stimulation of the anterior capsule included the striatum (adjacent to the electrode), the pons and cortical foci in the frontal, occipital and temporal lobes. Changes of site of electrical stimulation are clearly reflected by changes in signals on fMRI.

The above results show that bilateral electrical stimulation in the anterior limbs of the internal capsules induces a significant decrease in the Y-BOCS. As shown by fMRI in one patient, it appears that the neuronal substrate of electrical stimulation of the anterior capsule included the striatum (adjacent to the electrode), the pons and cortical foci in the frontal, occipital and temporal lobes. Changes of site of electrical stimulation are clearly reflected by changes in signals on MRI.

Electrical capsular stimulation in OCD patients is attractive from an ethical standpoint for its reversible character. Furthermore, it allows randomized and blinded clinical studies in a field where previously this proved to be very difficult, due to the irreversibility of brain lesioning. However, a lesioning procedure could still be performed if capsular stimulation was not successful.

Our observations in five of the six patients clearly show at least some beneficial effects during electrical stimulation in the anterior limbs of the internal capsules. These effects were clearly demonstrated in at least the three patients who had a follow-up of at least 21 months. But as a reversible alternative for capsulotomy, electrical stimulation of the anterior limbs of the internal capsules may become a more acceptable last-resort option for treatment-refractory, severely suffering OCD patients.

The invention, as described, does not depend upon using a physiological signal as a means to provide feedback to the patient to adjust stimulation parameters or upon a co-treatment by means of drugs such as GABA agonists. Further, the invention described herein has been described with certain parameters and limitations. These parameters and limitations have been given to describe the best mode for practicing the invention but are not intended to limit the scope of the invention. Thus, embodiments of the method for treating obsessive-compulsive disorder with electrical stimulation of the brain internal capsule are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
   delivering a stimulation signal from an implanted electrical signal generator to a structure within a brain via a plurality of electrodes implanted within the structure; and
   configuring each of the electrodes to have the same polarity to deliver the stimulation signal substantially parallel to axons within the structure,
   wherein the plurality of electrodes are located on a distal portion of a lead, the method further comprising implanting the distal portion within the structure substantially perpendicular with the axons.

2. The method of claim 1, further comprising configuring each of the electrodes as a cathode.

3. The method of claim 1,
   wherein the lead comprises a first lead and the plurality of electrodes comprises a first plurality of electrodes located on the first lead, and
   wherein configuring the electrodes to deliver the stimulation signal substantially parallel to axons within the structure comprises configuring each of the first plurality of electrodes as a cathode and each of a second plurality of electrodes implanted within the structure on a second lead as an anode to deliver the stimulation signal from the first plurality of electrodes to the second plurality of electrodes.

4. The method of claim 1, wherein delivering a stimulation signal to a structure comprises delivering the stimulation signal to anisotropic tissue of the brain.

5. The method of claim 1, wherein delivering a stimulation signal to a structure comprises delivering the stimulation signal to an internal capsule of the brain.

6. The method of claim 5, wherein delivering a stimulation signal to a structure comprises delivering the stimulation signal to an anterior portion of the internal capsule.

7. The method of claim 1, wherein delivering a stimulation signal to a structure comprises delivering the stimulation signal to a head of a caudate nucleus of the brain.

8. The method of claim 1, wherein delivering a stimulation signal to a structure comprises delivering the stimulation signal to a putamen of the brain.

9. The method of claim 1, wherein delivering a stimulation signal to a structure comprises delivering the stimulation signal to a nucleus accumbens of the brain.

10. The method of claim 1, wherein delivering a stimulation signal to a structure comprises delivering the stimulation signal to a ventral striatum of the brain.

11. The method of claim 1, wherein delivering a stimulation signal comprises delivering the stimulation signal to treat an obsessive disorder.

12. The method of claim 1, wherein delivering a stimulation signal comprises delivering the stimulation signal to treat a compulsive disorder.

13. The method of claim 1, wherein delivering a stimulation signal comprises delivering the stimulation signal to treat anxiety 14. The method of claim 1, wherein delivering a stimulation signal comprises delivering the stimulation signal to treat depression.

15. A method comprising:
delivering a stimulation signal from an implanted electrical signal generator to a structure within a brain via a plurality of electrodes implanted within the structure; and
configuring the electrodes to deliver the stimulation signal substantially parallel to axons within the structure,
wherein the plurality of electrodes comprises a first electrode located on a first lead and a second electrode located on a second lead, and configuring the electrodes to deliver the stimulation signal substantially parallel to axons within the structure comprises configuring the first electrode as a cathode and the second electrode as an anode to deliver the stimulation signal from the first electrode to the second electrode, and
wherein the first and second electrodes are located on respective first and second distal portions of the first and second leads, the method further comprising implanting the distal portions within the structure substantially perpendicular with the axons.

16. A method comprising:
configuring at least one of a plurality of electrodes as an anode;
configuring at least one other of the plurality of electrodes located ventrally relative to the anode as a cathode; and
delivering a stimulation signal through the at least one anode and at least one cathode to a structure within a brain of a patient, the stimulation signal configured to provide the patient with at least a partial relief from at least one of an obsession, compulsion, anxiety, or depression disorder,
wherein the structure comprises at least one of an internal capsule, a head of a caudate nucleus, a putamen, a nucleus accumbens, or a ventral striatum.

17. The method of claim 16, wherein delivering a stimulation signal comprises delivering the stimulation signal to the internal capsule.

18. The method of claim 17, wherein delivering a stimulation signal comprises delivering the stimulation signal to an anterior portion of the internal capsule.

19. The method of claim 18, wherein delivering a stimulation signal comprises delivering the stimulation signal to disrupt neural activity within a Meyerson lesion area within the anterior portion of the internal capsule.

20. The method of claim 16, wherein delivering a stimulation signal comprises delivering the stimulation signal to the head of a caudate nucleus.

21. The method of claim 16, wherein delivering a stimulation signal comprises delivering the stimulation signal to the putamen.

22. The method of claim 16, wherein delivering a stimulation signal comprises delivering the stimulation signal to the nucleus accumbens.

23. The method of claim 16, wherein delivering a stimulation signal comprises delivering the stimulation signal to the ventral striatum.

24. The method of claim 16, wherein delivering a stimulation signal comprises delivering the stimulation signal to treat an obsessive disorder.

25. The method of claim 16, wherein delivering a stimulation signal comprises delivering the stimulation signal to treat a compulsive disorder.

26. The method of claim 16, wherein delivering a stimulation signal comprises delivering the stimulation signal to treat anxiety.

27. The method of claim 16, wherein delivering a stimulation signal comprises delivering the stimulation signal to treat depression.

28. The method of claim 16, wherein delivering a stimulation signal comprises bilaterally delivering stimulation signals to corresponding structures located within respective hemispheres of the brain.

* * * * *

UNITED STATES PATENT AND TRADEMARK OFFICE
CERTIFICATE OF CORRECTION

| | | |
|---|---|---|
| PATENT NO. | : 7,616,998 B2 | Page 1 of 1 |
| APPLICATION NO. | : 10/888807 | |
| DATED | : November 10, 2009 | |
| INVENTOR(S) | : Nuttin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1084 days.

Signed and Sealed this

Nineteenth Day of October, 2010

David J. Kappos
*Director of the United States Patent and Trademark Office*